US009189604B2

(12) United States Patent
Lawandy

(10) Patent No.: US 9,189,604 B2
(45) Date of Patent: Nov. 17, 2015

(54) GAS ACTIVATED CHANGES TO LIGHT ABSORPTION AND EMISSION CHARACTERISTICS FOR SECURITY ARTICLES

(71) Applicant: Nabil Lawandy, Saunderstown, RI (US)

(72) Inventor: Nabil Lawandy, Saunderstown, RI (US)

(73) Assignee: SPECTRA SYSTEMS CORPORATION, Providence, RI (US)

( * ) Notice: Subject to any disclaimer, the term of this patent is extended or adjusted under 35 U.S.C. 154(b) by 123 days.

(21) Appl. No.: 14/179,833

(22) Filed: Feb. 13, 2014

(65) Prior Publication Data

US 2014/0159860 A1    Jun. 12, 2014

Related U.S. Application Data

(63) Continuation-in-part of application No. 13/021,412, filed on Feb. 4, 2011, now Pat. No. 9,075,020.

(60) Provisional application No. 61/301,340, filed on Feb. 4, 2010.

(51) Int. Cl.
| | |
|---|---|
| *G01N 21/64* | (2006.01) |
| *G06F 21/00* | (2013.01) |
| *G01N 21/78* | (2006.01) |
| *G07D 7/12* | (2006.01) |

(52) U.S. Cl.
CPC ............. *G06F 21/00* (2013.01); *G01N 21/643* (2013.01); *G01N 21/6408* (2013.01); *G01N 21/783* (2013.01); *G07D 7/122* (2013.01); *G01N 2021/6417* (2013.01); *G01N 2021/6439* (2013.01)

(58) Field of Classification Search
CPC combination set(s) only.
See application file for complete search history.

(56) References Cited

U.S. PATENT DOCUMENTS

| 3,220,549 | A | * | 11/1965 | Wong | 209/534 |
| 4,146,792 | A | * | 3/1979 | Stenzel et al. | 250/365 |
| 4,455,039 | A | * | 6/1984 | Weitzen et al. | 283/83 |
| 5,450,065 | A | * | 9/1995 | Greenfield | 340/584 |
| 5,789,754 | A | * | 8/1998 | Cathey et al. | 250/372 |
| 6,025,200 | A | * | 2/2000 | Kaish et al. | 436/56 |
| 6,232,124 | B1 | * | 5/2001 | Selinfreund | 436/20 |

(Continued)

FOREIGN PATENT DOCUMENTS

WO        0038283        6/2000

OTHER PUBLICATIONS

PCT International Search Report for PCT/US2011/023767 mailed Apr. 1, 2011.

(Continued)

*Primary Examiner* — Jennifer Mehmood
*Assistant Examiner* — Rufus Point
(74) *Attorney, Agent, or Firm* — Barlow, Josephs & Holmes, Ltd.

(57) ABSTRACT

Disclosed are security articles and methods and systems for authenticating security articles using a plurality of stimuli. According to one embodiment, an illustrative security feature includes an encoded feature wherein differential activation of phosphorescent or fluorescent materials creates a machine readable code through the simultaneous presence of a source of electromagnetic radiation and a specific gas environment. A detector detects a differential spectral emission across the security feature that results from the change in gas environment. The spectral emission may be compared to an expected emissive signature to determine authenticity of the security article.

14 Claims, 7 Drawing Sheets

(56) References Cited

U.S. PATENT DOCUMENTS

| | | | |
|---|---|---|---|
| 6,528,318 B1* | 3/2003 | Miragliotta et al. | 436/56 |
| 7,089,420 B1* | 8/2006 | Durst et al. | 713/176 |
| 7,315,377 B2* | 1/2008 | Holland et al. | 356/419 |
| 7,381,972 B1* | 6/2008 | Varmette et al. | 250/458.1 |
| 7,531,108 B2* | 5/2009 | Hampden-Smith et al. | 252/301.36 |
| 7,773,749 B1* | 8/2010 | Durst et al. | 380/54 |
| 8,121,386 B2* | 2/2012 | Rancien | 382/141 |
| 8,139,901 B2* | 3/2012 | Kanevsky et al. | 382/306 |
| 8,220,716 B2* | 7/2012 | Mercolino | 235/491 |
| 8,247,018 B2* | 8/2012 | Mercolino | 427/2.1 |
| 8,277,612 B2* | 10/2012 | Kane et al. | 162/181.1 |
| 8,458,475 B2* | 6/2013 | Mercolino | 713/176 |
| 8,558,995 B2* | 10/2013 | Doublet | 356/71 |
| 2003/0035972 A1* | 2/2003 | Hanson et al. | 428/480 |
| 2004/0022355 A1* | 2/2004 | Kaiser et al. | 378/49 |
| 2005/0109983 A1* | 5/2005 | Pai-Paranjape et al. | 252/299.01 |
| 2005/0172852 A1* | 8/2005 | Anderson et al. | 106/31.03 |
| 2006/0028727 A1* | 2/2006 | Moon et al. | 359/569 |
| 2006/0086803 A1* | 4/2006 | Berson | 235/491 |
| 2006/0228802 A1* | 10/2006 | Tiller et al. | 436/56 |
| 2006/0285108 A1* | 12/2006 | Morrisroe | 356/316 |
| 2007/0023521 A1* | 2/2007 | Wildey et al. | 235/454 |
| 2008/0151248 A1* | 6/2008 | Cole et al. | 356/437 |
| 2009/0033914 A1* | 2/2009 | Doublet | 356/71 |
| 2010/0090845 A1* | 4/2010 | Polak et al. | 340/632 |
| 2010/0208313 A1* | 8/2010 | Horgan et al. | 359/2 |
| 2010/0291618 A1* | 11/2010 | Robinson et al. | 435/34 |
| 2010/0304491 A1* | 12/2010 | McNeil | 436/56 |
| 2011/0127446 A1* | 6/2011 | Star et al. | 250/459.1 |
| 2011/0193335 A1* | 8/2011 | Budd et al. | 283/75 |
| 2011/0261999 A1 | 10/2011 | Kanevsky et al. | |
| 2012/0140791 A1* | 6/2012 | Lawandy | 374/45 |

OTHER PUBLICATIONS

PCT Written Opinion of the International Searching Authority for PCT/US2011/023767 mailed Apr. 1, 2011.

* cited by examiner

GAS ACTIVATED CHANGES TO LIGHT ABSORPTION AND EMISSION CHARACTERISTICS FOR SECURITY ARTICLES

CROSS-REFERENCE TO RELATED APPLICATIONS

This application is a continuation-in-part of earlier filed U.S. patent application Ser. No. 13/021,412, filed Feb. 4, 2011 which claims priority from earlier filed U.S. Provisional Application No. 61/301,340, filed Feb. 4, 2010.

BACKGROUND OF THE INVENTION

The present invention relates generally to detectable security markings. More specifically, the present invention relates to security articles having light absorption and emission characteristics that change upon exposure to a specific gas environment.

Counterfeiting and forgery have become significant concerns in the modern economy and marketplace. Advances in computing technology and printing techniques have increased the incidence of forgeries, counterfeited documents, and other fraudulent activities. Countless areas of today's high-technology society require and rely upon certification, authentication and protection of highly valuable documents, papers, currency and other materials. Thus, there is a need for security markings to be incorporated into currency, important documents, packaging, and other authentic materials to prevent unauthorized copying, forging, counterfeiting and other fraudulent use.

A similar problem exists in a variety of contexts. In addition to protecting against counterfeit currency, authentication of valuable documents or materials also affects many facets of the economy. Authentication stamps such as visas or postmarks, for example are subject to fraudulent use and forgery. Also a wide variety of products and consumer goods may be created as knock-offs cheap replacements or gray market goods. Notaries public use a raised stamp to authenticate notarized documents. Drivers' licenses, passports and other photographic identification contain holograms and microprinting. Sporting memorabilia and retail clothiers use holographic tags and stamps to assist in proving authenticity. Even fashion designers are now including authentication devices in their clothing to prevent passing off of knock-offs as designer products.

Current methods of authentication of currency involve visual observation, scanning under ultraviolet lamps, notes containing security threads, and emissive materials such as inks and planchettes. Such security threads emit a distinct marking, color or code in response to exposure to the ultraviolet light. In some circumstances, the emissive features of different denominations of notes can emit different colors. In addition to the colors of the emission, a code number or other unique identifier can be detected by the naked eye when the note is exposed to ultraviolet light or excitation of some form.

A disadvantage to most of the traditional security features is that they are visible and known to the world. If a counterfeiter is aware there is a security thread in a bill or a watermark in a document, replication of the security feature is easier. Once a feature is made known to the public, a counterfeiter may begin to develop specific strategies and solutions to overcome the security protections provided by the specific feature. Methods of creating and perfecting forgeries and counterfeit documents have become easier and more available with the advent of highly sophisticated computer printing and processing. As far back as 1991, the United States Treasury has continually added security safeguard features to the denominations of currency in an attempt to combat the use of counterfeit money. These safeguards have included watermarks, security threads embedded in the paper, microprinting, color-shifting ink, and the use of multi-colored bills.

Accordingly, a need exists for security features that further reduce a counterfeiter's likelihood of success, even if they are aware of the existence of the security feature. There is a further need for covert optically encoded markings, formed from at least one emitter that responds differently when exposed to two varied stimuli to create a machine readable response that cannot be detected by the human eye.

BRIEF SUMMARY OF THE INVENTION

Embodiments of the invention include security articles and methods and systems for authenticating security articles using a plurality of stimuli. According to one embodiment, an illustrative security feature includes activation of phosphorescent or fluorescent materials by the simultaneous presence of a source of electromagnetic radiation and a specific gas environment. Thus, the radiation and gas serve as first and second stimuli.

Security articles, such as those described herein, may require more than one stimulus, e.g., application of both light and a gas environment, to detect the authentication feature. Further, such security articles may have security features that can be used either publicly, covertly, or both, i.e., having a first response for public access and a second response for covert usage.

In one embodiment, the invention relates to a security article. The security article can include a host material comprising a gas-activated security feature incorporated upon or within the host material, wherein the gas-activated security feature is capable of emitting a spectral emission that changes upon exposure to a change in gas environment of the gas-activated security feature. The host material may include a polymer. The host material may include a responsive portion and a non-responsive portion, wherein the gas-activated security feature may be incorporated upon or within the responsive portion. The host material may include a reference security feature. In such a case, the security feature and the reference security feature may emit different spectral emissions upon exposure to the change in gas environment. Also, in such a case, the security feature and the reference security feature may emit equivalent spectral emissions upon exposure to the change in gas environment.

The gas-activated security feature may include a material selected from the group consisting of fluorescent material and environment source for initiating a change in gas environment of the gas-activated security feature; and a detector for detecting a spectral emission of the gas-activated security feature resulting from the change in gas environment. The electromagnetic radiation source may include wavelengths selected from the group consisting of infrared, visible, and ultraviolet. The gas environment source may provide a gas environment selected from the group consisting of inert gas, water vapor, oxygen, carbon dioxide, chemical vapors, and human breath. The gas environment source may provide a gas environment by change in pressure or density, or by application of a vacuum. The detector system may further include a gas environment altering device that removes gas from or injects gas into the gas environment. The detector may be a spectrometer.

BRIEF DESCRIPTION OF THE DRAWINGS

These embodiments and other aspects of this invention will be readily apparent from the detailed description below and the appended drawings, which are meant to illustrate and not to limit the invention, and in which.

DETAILED DESCRIPTION OF THE INVENTION

Figure 1:
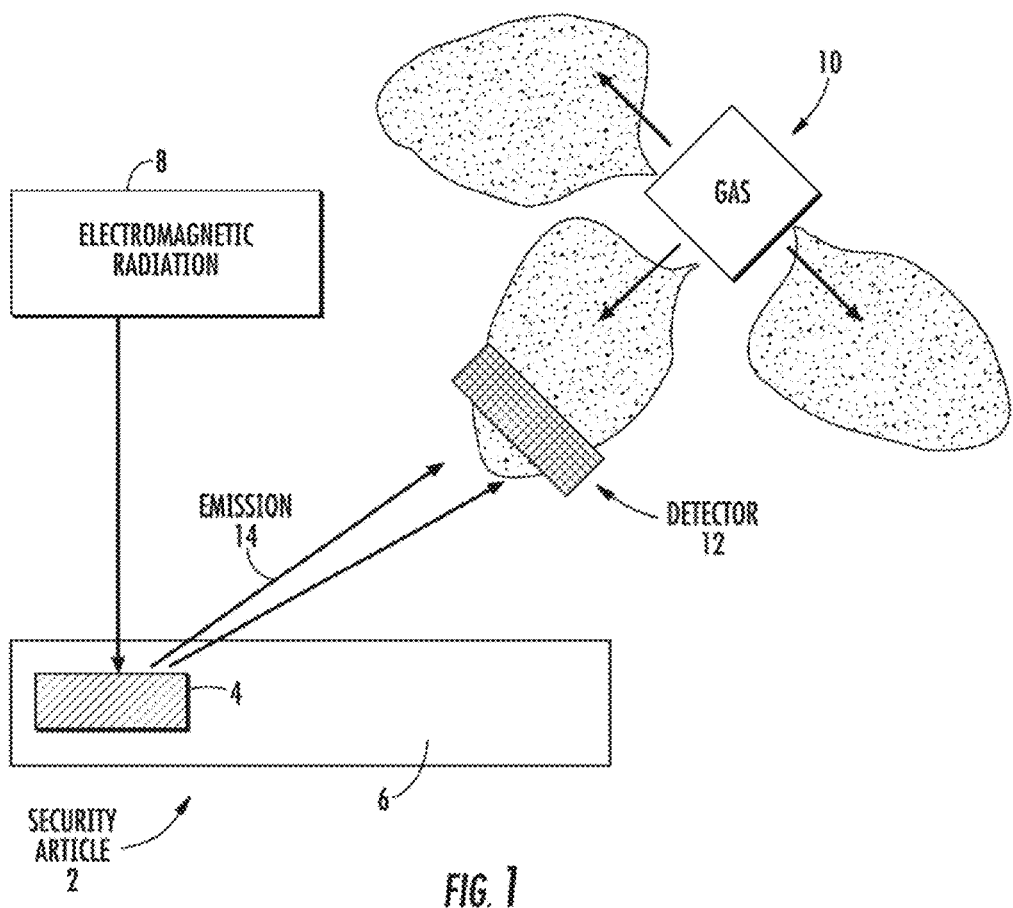
FIG. 1 is an illustrative embodiment of the invention showing a security article, an electromagnetic radiation source, a gas environment source, and a detector in accordance with an embodiment of the invention.

The invention will be more completely understood through the following detailed description, which should be read in conjunction with the attached drawings. While detailed embodiments of the invention are disclosed herein, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the invention in virtually any appropriately detailed embodiment.

Embodiments of the invention include fluorescent or phosphorescent emissions from a security article upon the application of a specific gas environment. Specifically, application of a particular gas reveals unique spectral signatures of a security article. In one embodiment, exposing the security article to a gaseous excitation, i.e., a specific gas environment, reveals a unique spectral emission by which the security article may be authenticated. According to embodiments of the invention, excitation of the security article may include visible ambient light or sunlight, or may include other light or electromagnetic sources such as ultraviolet sources or infrared sources.

The specific gas environment to which the security article may be exposed may include both a responsive gaseous portion, which is capable of causing changes to the absorption or excitation of the security feature, and a non-responsive gaseous portion, which does not cause such a response to the security feature. According to one embodiment of the invention, the gas used for excitation may be a non-toxic, safe-exposure gas, such as an inert gas. According to other embodiments, the responsive gaseous portion may include water vapor, oxygen, carbon dioxide or other chemical vapors, or human breath, which has depleted oxygen levels compared to the atmosphere. Further, the responsive gaseous portion may be the result of a change in the gas environment, such as a pressure or density change, e.g., by creating a vacuum.

The security article may include one or more gas sensitive materials, which may be disposed on or within a permeable host material, such as a polymer material. The gas sensitive material of the security article may be part of an ink, a coating, a security thread, a planchette, a particle, a hologram, or a windowed region in a document or banknote. The light emission spectrum of the security article can extend from the ultraviolet to the infrared, depending on the gas environment. The excitation response of the gas sensitive material is a result of the types of molecules used, the bonding capabilities of the material to a host material, and the permeability of the material to various gas constituents of the host material.

The absorption characteristics of the gas sensitive material change with exposure to a specific gas environment. The change in the absorption characteristics may result in a change of the visible color of the gas sensitive material. The changes in the absorption characteristics may result with or without the application of sources of light or electromagnetic radiation in addition to or instead of ambient light or sunlight. The light emission or color of the gas sensitive material may change upon excitation with a stimulus from an electromagnetic source, e.g., ultraviolet, visible or infrared. Thus, authenticity of a security article may be determined by measuring the intensity of the security feature's spectral emission or change thereof.

In addition, the gas sensitive material may have the characteristic that it changes color upon a stimulus from an electromagnetic source and has a relaxation or rate of change back to its original color determined by the gas environment. In other words, the light emission of the gas sensitive material may have a lifetime that depends on the specific gas environment or changes to the gas environment. The gas-activated security feature may be in (1) an original state prior to application of electromagnetic radiation and/or a gas environment, (2) a gas-activated state simultaneous with or after application of electromagnetic radiation and/or a gas environment, or (3) reversion to an original state after application of electromagnetic radiation and/or a gas environment. The spectral emission may respond differently in the original, activated, and reversionary states. Thus, authenticity of a security article may also be determined by measuring fluorescence lifetime, i.e., a time response of the security feature's spectral emission or change thereof.

A detector system for analyzing the security features in a security article may include an electromagnetic or light excitation source, a device for spectral detection of absorption, color or emission, and a gas environment altering device, such as a pump, nozzle or jet from a gas source. The gas environment altering device may suck air away from around the security article or may blow a specific gas composition onto the security article. Alternatively, the gas environment altering device may include a straw-like device for blowing human breath onto the article. The detector system may also be capable of measuring the time response of the phase responses of spectral changes of the security article, e.g., with respect to periodic excitation by light or a gas environment.

The spectral emissions of a security article may be used to identify and verify the authenticity of the article. A spectral emission may be illustrated by showing the intensity of the feature as a function of wavelength. A spectral emission from a typical security feature yields a signature having detectable characteristics or patterns across the wavelength spectrum. According to one embodiment of the invention, the security feature is enhanced such that excitation of the feature creates a distinct spectral pattern that may be analyzed to verify authenticity. If, upon scanning the spectral emission of the article containing the feature, the expected emissive signature does not match an expected signature, the article may be a forgery or may have been tampered with. If the signature matches the expected pattern or value, the document may be authentic.

FIG. 1 is an illustrative embodiment of the invention showing a security article, an electromagnetic radiation source, a gas environment source, and a detector. The security article 2 has a gas-activated security feature 4 incorporated upon or within a host material 6. An electromagnetic radiation source 8 directs electromagnetic radiation to the security article 2 having a gas-activated security feature 4. A gas environment source 10 initiates a change in gas environment of the security feature 4. A detector 12 detects a spectral emission 14 that results from the change in gas environment and/or simultaneous or subsequent exposure to electromagnetic radiation.

Figure 2:
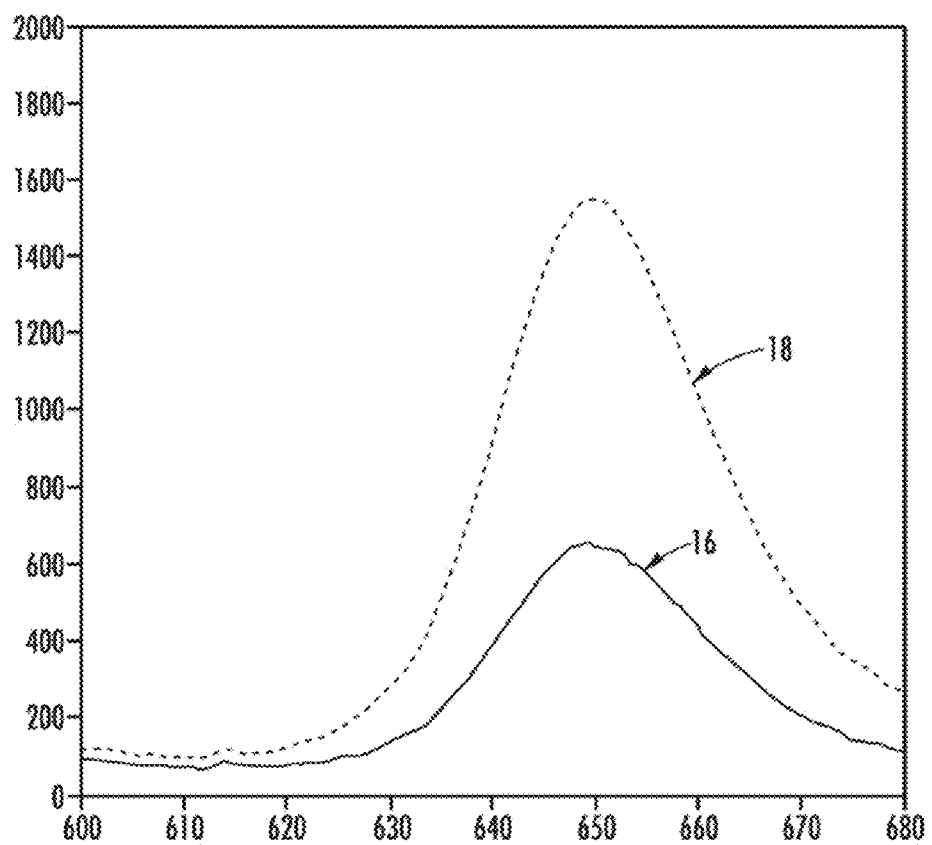
FIG. 2 is an illustrative graph of the spectral emission of a security article in accordance with an embodiment of the invention.

FIG. 2 shows a spectral emission signature of a security feature in accordance with an embodiment of the invention. Specifically, FIG. 2 depicts the intensity of an emissive response from two excitation forms—one optical, one optical and gaseous—as a function of wavelength. A first spectral signature 16 is the result of optical excitation of the security feature; application of the optical excitation results in a higher emission over certain wavelengths. A second spectral signature 18 results from the excitation of the security feature with optical and gaseous exposure simultaneously. As shown in the graph of FIG. 2, the spectral signature of the excitation including a specific gas environment results in a significantly higher emissive response. A detector system, such as a spectrometer, may easily read the higher intensity of the security article's emission as part of the authentication process.

Figure 3:
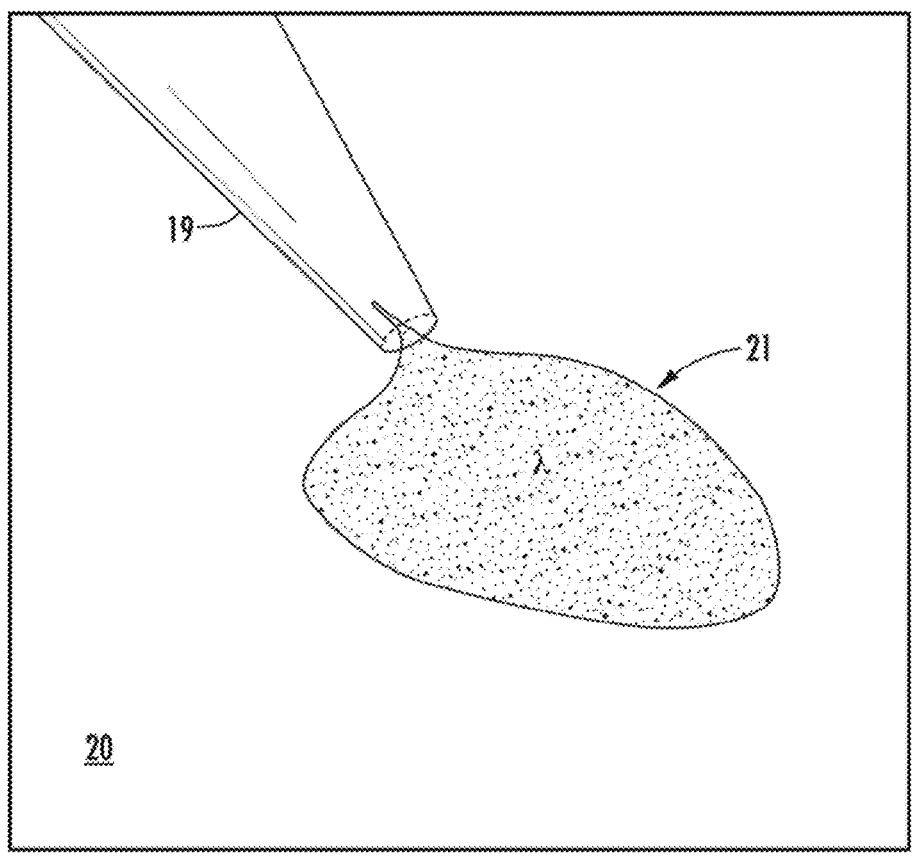
FIG. 3 depicts the application of a gas environment to a security article in accordance with an embodiment of the invention.

FIG. 3 depicts the application of an optical and gaseous excitation to a phosphorescent material. When exposed to ultraviolet light or another type of electromagnetic radiation and a specific gas from a jet 19, the phosphorescent material 20 exhibits a detectable intensity 21 in the region λ to which the light and gas are applied.

Figure 4:
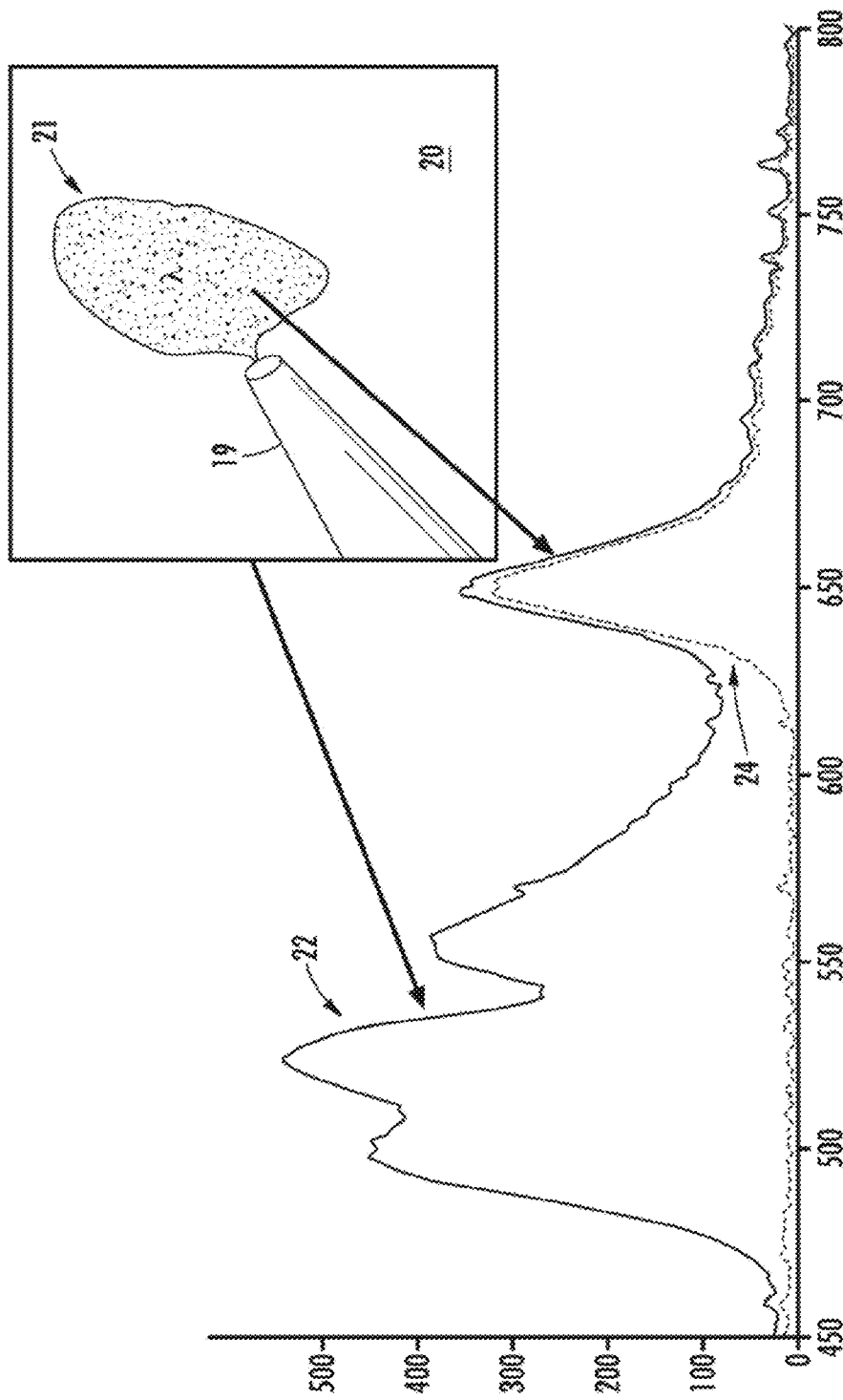
FIG. 4 is an illustrative graph of the spectral emission of a security article in accordance with an embodiment of the invention.

According to another embodiment of the invention, dual excitation materials or coatings may be included within existing phosphorescent or fluorescent emissive security features. FIG. 4 depicts a spectral graph (intensity versus wavelength) in accordance with an embodiment of the invention. A first spectral signature 22 exhibits a unique signature under optical and gaseous excitation. The first spectral emission of a chromophore, for example, yields a signature having unique and definable features at given wavelengths. In the example shown in FIG. 4, dips (absorption) and peaks (emissions) in the spectral emission occur at a certain wavelengths. These dips and peaks are undetectable to the human eye; however, the feature is machine readable, requiring only the use of a spectrometer or other detector system. A second spectral emission 24 shows the effect of the non-responsive portions of the gas environment, thus highlighting the additional spectral signature, i.e., measurable and quantifiable spectral shifts, obtained upon application of optical and gaseous excitation in spectral signature 22.

According to an embodiment of the invention, a machine-detectable security feature is included in a security article such as a document, currency, or secondary packaging for items such as tobacco, luxury goods, or pharmaceuticals. The security feature may be, e.g., embedded within a security thread, planchette or as part of an ink, resulting in a visible change of the excited signature of the threads when viewed using an ultraviolet source or lamp or other appropriate excitation source. Application of a specific gas environment, however, may lead to both a color change in the security feature as well as measurable and quantifiable spectral shifts, as shown in FIG. 4. The security feature, while undetectable to the naked eye under some circumstances, emits a specific and distinct color as well as a unique spectral fingerprint under optical and gaseous excitation in a specific gas environment. Choices in different phosphors lead to different color and spectral emissions. The incorporation of a machine readable, covert feature may be implemented without any change to the public perception of the excited emission signature, thereby making forgery or duplication of the document more difficult.

Figure 5:
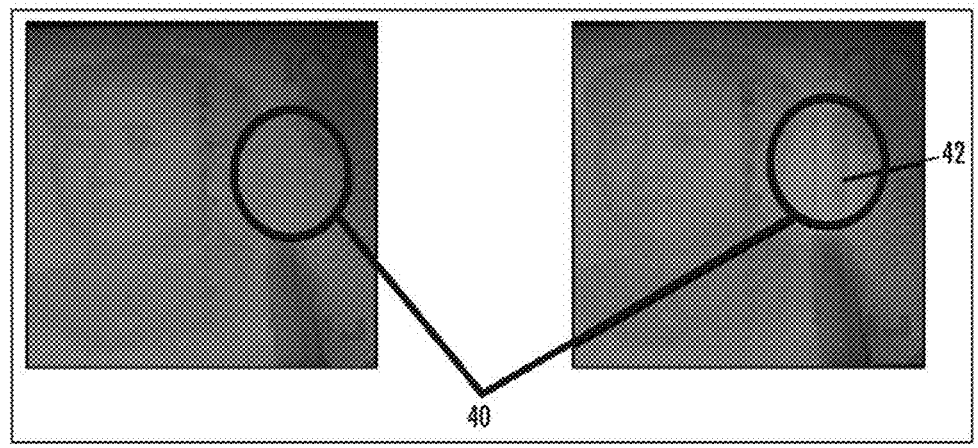
FIG. 5 depicts the application of a gas environment to a security article in accordance with an alternate embodiment of the invention.

In another embodiment a security feature may be altered by over coating the feature with a gas impermeable ink as shown in FIG. 5. First a security feature 40 having an emissive property is printed using a gaschromic ink as described above. The feature 40 is then over printed with a clear, oxygen impermeable ink to form a pattern. Due to the properties of the gaschromic ink, the overprinted layer 42 produces excitation contrast in the underlying feature when the gas environment surrounding the feature changes, i.e. when oxygen is introduced or removed. Other patterning may be achieved by also including spectrally identical emitters that are not gasochromic in order to create solid images that will reveal encoded information upon changes in molecular oxygen.

Figure 6:
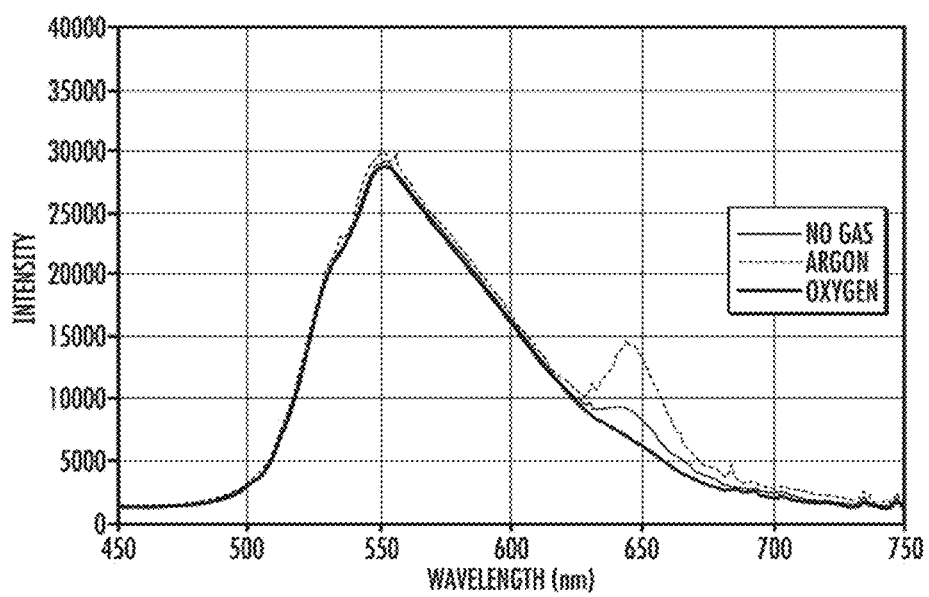
FIG. 6 is an illustrative graph of the spectral emission of a security article in accordance with the alternate embodiment of FIG. 5.

Using such a system, an existing emissive security feature that is already in use as a public feature can be modified to include a covert feature. A thin layer of gasochromic material can be overlayed onto an existing security feature. Further, a simple barcode can also be overlayed onto the combined system using a clear gas impermeable ink. The emission spectrum of the modified security feature in FIG. 6, contains the emission of the existing security feature along with the gasochromic compound in the thin ink overlay. The emission data also shows the response of the feature when exposed to $O_2$ and to Ar. The emission of the existing security feature is extremely stable and is insensitive to changes in the atmospheric environment while the characteristic emission of the gasochromic emission exhibits the expected behavior.

Figure 7:
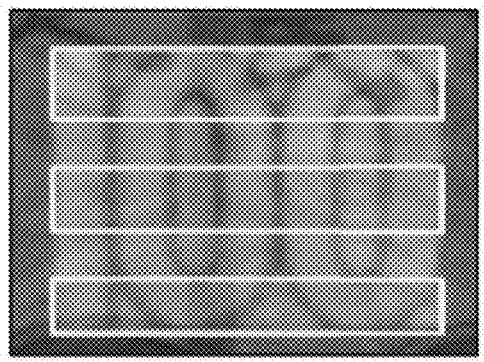
FIG. 7 depicts the application of a barcode feature to a security article in accordance with an alternate embodiment of the invention.
Figure 8:
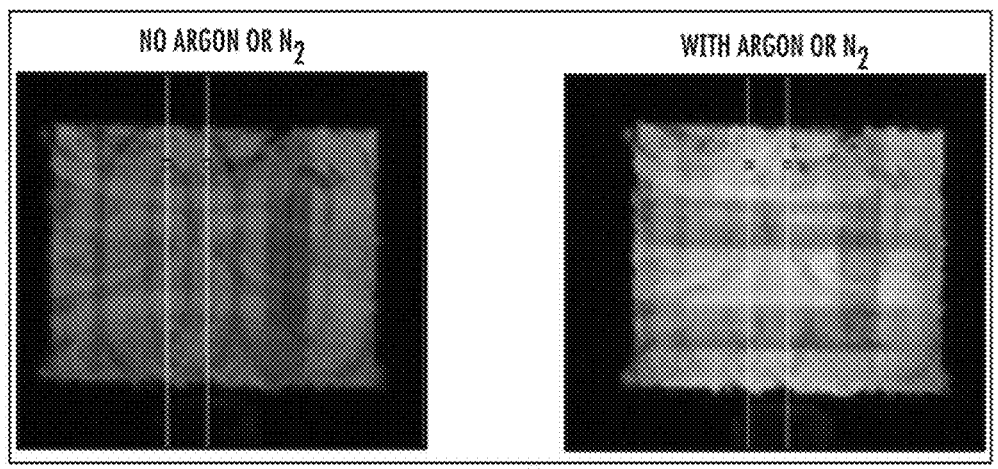
FIG. 8 depicts the response of the feature of FIG. 7.

As described above, a security feature can be coated with a gaschromic material and then masked and over printed with a thin coating of a gas oxygen impermeable ink in order to create a barcode pattern. An exemplary pattern is shown in FIG. 7. The areas where the boxes appear are where the gasochromic ink was not over coated and therefore remains active to reveal the bar code after filtering and image processing. The barcode was immediately apparent in the presence of Ar and/or $N_2$ gas streams as shown in FIG. 8.

Figure 9:
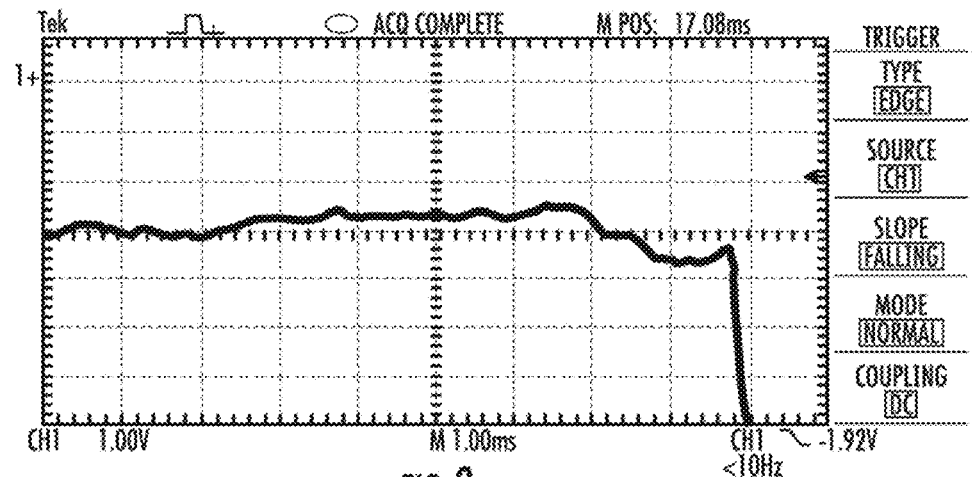
FIGS. 9-10 depict a machine verification response.
Figure 10:
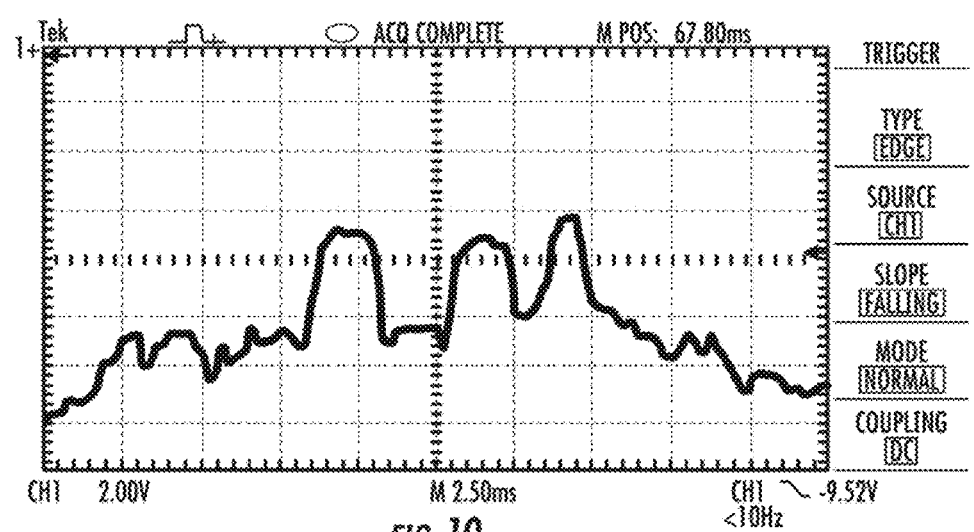

The security feature is also suited for high speed machine verification where FIG. 9 shows the signals obtained in the absence of gas and at 10 m/sec transport speed. While FIG. 10 depicts a response when a very low gas flow of $N_2$ was incident on the UV illumination side of the note. This remarkable result shows the world's first and only demonstration of a gas activated banknote security feature, fully hidden, and measured at high transport speeds.

There are various classes of compounds that may exhibit either an increase or decrease of electromagnetic radiation emission, intensity changes, fluorescence, or other detectable changes upon exposure to a specific gas environment. For example and without limitation, in one embodiment, the following classes of compounds may be gas-activated in an oxygen environment or other gas environment: platinum(II) or palladium(II) porphyrins; platinum(II) or palladium(II) phthalocyanines or naphthalocyanines; ruthenium(II) tris-bipyridine type complexes; terbium(III) assorted complexes; and perylene dyes. For example and without limitation, in another embodiment, the following classes of compounds may be gas-activated in a carbon dioxide environment or other gas environment: hydroxypyrene trisulfonic acid ("HPTS") in wet polymer or sol-gel media. For example and without limitation, in a further embodiment, the following classes of compounds may be gas-activated in a water environment or other type of environment: ruthenium(II) trisbipyridine type complexes; perylene dyes; and Reichardt's dye. In one embodiment, a water sensitive absorber can be used to selectively block absorption or emission from a fluorescent dye or other type of dye that is unaffected by water.

While embodiments of the invention disclosed herein describe detection of emissive features under the excitation of light and gas sources, one skilled in the art should recognize that advantages of the absorptive properties of a gas sensitive material may be utilized as a security feature. For example, according to another embodiment of the invention, a security feature may include phosphorescent material having an absorptive spectral response at certain wavelengths under optical excitation. Application of a gaseous excitation to the material results in the recovery of the emissive intensity of the material.

While embodiments of the invention disclosed herein describe detection based on specific responses to excitation sources, one skilled in art should recognize that additional parameters may be incorporated, such as the temporal decay of emissions, the spectral signature of the host, and response time and change in emission under gaseous excitation, without deviating from the scope of the invention.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be anyone of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

While the invention has been described with reference to illustrative embodiments, it will be understood by those skilled in the art that various other changes, omissions and/or additions may be made and substantial equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed:

1. A security article, comprising:
   a host material comprising a gas-activated security feature that emits at different wavelengths when exposed to changes in gas environment incorporated upon or within the host material; and
   a gas impermeable layer selectively applied over said gas-activated security feature leaving portions of said gas-activated security feature exposed,
   wherein the gas-activated security feature emits a first spectral emission that changes to a second spectral emission as said exposed portions upon exposure to a change in gas environment of the gas activated security feature.

2. The security article of claim 1 wherein the host material comprises a polymer.

3. The security article of claim 1 wherein the host material comprises a responsive portion and a non-responsive portion, and wherein the gas-activated security feature is incorporated upon or within the responsive portion.

4. The security article of claim 1 wherein the gas-activated security feature is further incorporated upon an existing security feature in an article.

5. The security article of claim 4 wherein the gas-activated security feature and the existing security feature emit different spectral emissions upon exposure to the change in gas environment.

6. The security article of claim 4 wherein the gas-activated security feature and the existing security feature emit equivalent spectral emissions upon exposure to the change in gas environment.

7. The security article of claim 1 wherein the gas-activated security feature comprises a material selected from the group consisting of fluorescent material and phosphorescent material.

8. The security article of claim 1 wherein the gas-activated security feature comprises a material selected from the group consisting of platinum(II) or palladium(II) porphyrins, platinum(II) or palladium(II) phthalocyanines or naphthalocyanines, ruthenium(II) tris-bipyridine type complexes, terbium (III) assorted complexes, perylene dyes, hydroxypyrene trisulfonic acid, Reichardt's dye, and combinations thereof.

9. A method of authenticating a security article, comprising the steps of:
   directing electromagnetic radiation to a security article comprising a gas-activated security feature having a gas impermeable layer selectively applied there over leaving portions of said gas-activated security feature exposed to create a first spectral emission in a first gas environment, initiating a change in gas environment of the security feature; and
   detecting a change from said first to a second spectral emission of the security feature resulting from the change in gas environment.

10. The method of claim 9 wherein the step of initiating a change in gas environment of the security feature comprises removing gas from or injecting gas into a first gas environment of the security feature to create a second gas environment of the security feature.

11. The method of claim 9 further comprising the step of comparing the differential spectral emission with an expected spectral emission to determine authenticity of the security article.

12. The method of claim 9 further comprising the step of measuring a time response of the spectral emission.

13. The method of claim 9 further comprising the step of changing the spectral emission of the security feature from an original state to a gas-activated state.

14. The method of claim 9 further comprising the step of changing the spectral emission of the security feature from a gas-activated state to an original state.

* * * * *